United States Patent
Endo et al.

(10) Patent No.: US 9,119,527 B2
(45) Date of Patent: Sep. 1, 2015

(54) IMAGE TRANSMITTING DEVICE AND IMAGE COMMUNICATION SYSTEM

(75) Inventors: Takahisa Endo, Tokyo (JP); Manabu Ishizeki, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 98 days.

(21) Appl. No.: 13/451,146

(22) Filed: Apr. 19, 2012

(65) Prior Publication Data

US 2012/0200688 A1 Aug. 9, 2012

Related U.S. Application Data

(63) Continuation of application No. PCT/JP2010/068577, filed on Oct. 21, 2010.

(30) Foreign Application Priority Data

Oct. 22, 2009 (JP) ................. 2009-243291

(51) Int. Cl.
  *H04N 7/18* (2006.01)
  *A61B 1/00* (2006.01)
  *H04W 72/08* (2009.01)

(52) U.S. Cl.
  CPC ......... *A61B 1/00016* (2013.01); *H04W 72/082* (2013.01)

(58) Field of Classification Search
  CPC ............ H04N 7/18; H04B 1/713; H04B 1/74; H04B 17/007; H04W 74/0808; H04W 72/085; H04L 1/20
  USPC .......................................................... 348/74
  See application file for complete search history.

(56) References Cited

U.S. PATENT DOCUMENTS

| 7,206,840 | B2 | 4/2007 | Choi et al. |
| 2002/0184122 | A1 | 12/2002 | Yamaguchi et al. |
| 2004/0196364 | A1 | 10/2004 | Takahashi |
| 2005/0185629 | A1 | 8/2005 | Kuroda et al. |

(Continued)

FOREIGN PATENT DOCUMENTS

| JP | 60-48011 A | 3/1995 |
| JP | 2004-520766 A | 7/2004 |

(Continued)

OTHER PUBLICATIONS

"IEEE Standard for Information technology—Telecommunications and information exchange between systems—Local and metropolitan area networks—Specific requirements Part 11: Wireless LAN Medium Access Control (MAC) and Physical Layer (PHY) Specifications," IEEE Std. 802. 11. Jun. 12, 2007, Revision of IEEE Std, pp. 1-1184.

(Continued)

*Primary Examiner* — Jay Patel
*Assistant Examiner* — Neil Mikeska
(74) *Attorney, Agent, or Firm* — Westerman, Hattori, Daniels & Adrian, LLP (57) ABSTRACT

An image transmitting device includes: a transmitting unit that transmits image data by wireless communication; a measuring unit that measures information relating to a busy state of a communication channel used in the wireless communication for a time period per 1 field of the image data; and a judging unit that judges a state of the communication channel based on a measurement result by the measuring unit.

4 Claims, 10 Drawing Sheets

(56) References Cited

U.S. PATENT DOCUMENTS

| | | |
|---|---|---|
| 2006/0056344 A1 | 3/2006 | Roy et al. |
| 2008/0137620 A1* | 6/2008 | Wang et al. .................. 370/337 |
| 2008/0139881 A1* | 6/2008 | Cover et al. .................. 600/103 |
| 2008/0320526 A1 | 12/2008 | Franceschini et al. |
| 2010/0061362 A1* | 3/2010 | Wang et al. .................. 370/350 |
| 2012/0079329 A1* | 3/2012 | Steinbach et al. ............ 714/704 |
| 2012/0157007 A1* | 6/2012 | Yoneyama et al. ........ 455/67.14 |

FOREIGN PATENT DOCUMENTS

| | | |
|---|---|---|
| JP | 2006-109448 A | 4/2006 |
| JP | 2006-271433 A | 10/2006 |
| JP | 2007-523503 A | 8/2007 |
| JP | 2009-159406 A | 7/2009 |
| JP | 2010-518745 A | 5/2010 |
| WO | 2008/097221 A1 | 8/2008 |
| WO | 2008/149639 A1 | 11/2008 |
| WO | 2009/104336 A1 | 8/2009 |

OTHER PUBLICATIONS

International Search Report of PCT/JP2010/068577, mailing date of Jan. 25, 2011.
Extended European Search Report dated Dec. 7, 2012, issued in corresponding European Patent Application 10825012.7 (9 pages).
Japanese Notice of Allowance dated Oct. 7, 2014, issued in corresponding JP Application No. 2009-243291 with English translation (6 pages).

* cited by examiner

| CH NO. (CH_NO) | COMMUNICATION CHANNEL GROUP | |
|---|---|---|
| | COMMUNICATION CHANNEL [PHYSICAL CHANNEL NO.] | ADJACENT CHANNELS [PHYSICAL CHANNEL NO.] |
| 1 | 1 | 2, 3, 4 |
| 2 | 6 | 3, 4, 5, 7, 8, 9 |
| 3 | 11 | 8, 9, 10, 12, 13 |

FIG. 11

| | | SEARCH ORDER (SCAN_NO) | | | | | | | |
|---|---|---|---|---|---|---|---|---|---|
| | | 1 | 2 | 3 | 4 | 5 | 6 | 7 | 8 |
| CH NO. (CH_NO) | 1 | 1 | 2 | 3 | 4 | 0 | 0 | 0 | 0 |
| | 2 | 6 | 3 | 4 | 5 | 7 | 8 | 9 | 0 |
| | 3 | 11 | 8 | 9 | 10 | 12 | 13 | 0 | 0 |

IMAGE TRANSMITTING DEVICE AND IMAGE COMMUNICATION SYSTEM

BACKGROUND OF THE INVENTION

1. Field of the Invention

The present invention relates to an image transmitting system that has an image transmitting device that transmits image data by means of wireless communication that uses a wireless communication format such as wireless LAN or the like, and an image receiving device that receives image data by means of wireless communication.

Priority is claimed on Japanese Patent Application No. 2009-243291, filed Oct. 22, 2009, the content of which is incorporated herein by reference.

2. Description of Related Art

In recent years, endoscope devices have come to be widely used that, by inserting a long narrow insertion unit into a body cavity or conduit, can observe with a monitor a subject image of the body cavity or conduit. This kind of endoscope device generally has an endoscope that has an insertion unit that is inserted in a body cavity or conduit, and a main body device that has a light source device and video processor. This endoscope and main body device are connected by a light guide cable that guides illumination light from the light source device to the endoscope, and a signal cable that transmits the image signal obtained by the endoscope to the video processor. Thereby, the range of movement of the endoscope was restricted and the operability of the endoscope was hindered.

Therefore, for example, in Japanese Unexamined Patent Application, First Publication S60-48011 (hereinbelow, referred to as Patent Document 1), an illumination device constituted by an LED (light-emitting diode) or the like is built into the endoscope. With this constitution, the light guide cable that extends from the endoscope is removed. Also, the endoscope is provided with a video signal processing circuit that obtains a video signal that can be shown on a monitor by performing a video signal process on the image signal, and a transmitting circuit that transmits this video signal via radio. Separately from the endoscope, a receiving device that receives the radio waves and demodulates the video signal is provided. With this constitution, the signal cable that extends from the endoscope is removed. This type of endoscope device is generally called a wireless endoscope device, and it has the advantages of the restrictions in the range of movement of the endoscope being eased, and the operability improving.

In the conventional wireless endoscope device, the receiving device is provided separately from the endoscope. Due to having such a structure, it is necessary to perform setting of the communication channel of the endoscope on the transmission side in accordance with the communication channel that is set in the receiving device, and to make a connection by wireless communication. A method is also conceivable of uniquely determining a combination of receiving device and endoscope, and setting the communication channel thereof in a fixed manner to an arbitrary channel in advance. However, in a hospital, a plurality of receiving devices and a plurality of endoscopes are used, and the disinfection/sterilization treatment of endoscopes and inspection are carried out simultaneously. For this reason, combinations of a receiving device and an endoscope are not uniquely determined Also, in order to prevent radio wave interference, the communication channels of the receiving devices need to be set to respectively differ.

Figure 13:
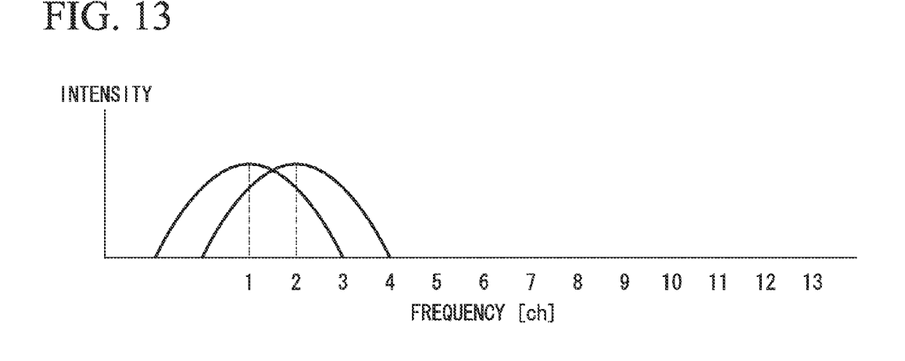
FIG. 13 is a reference diagram that shows frequency bands that communication channels use.

As the communication method that is used for wireless communication, it is effective to use a wireless communication method such as IEEE 802.11 that is used in wireless LANs in which high-speed data communication is possible. In this wireless communication method, in order to effectively use the frequency band, wireless communication can be performed by selecting an arbitrary channel from a plurality of channels. Each of the communication channels is arranged so that the usable frequency band partially overlaps with another communication channel as shown in FIG. 13, due to restrictions of the available frequency band. For this reason, at the start of operation, the endoscope device checks the status of use of available communication channels to determine the optimal communication channel, and starts wireless communication between the receiving device and the endoscope.

Figure 14:
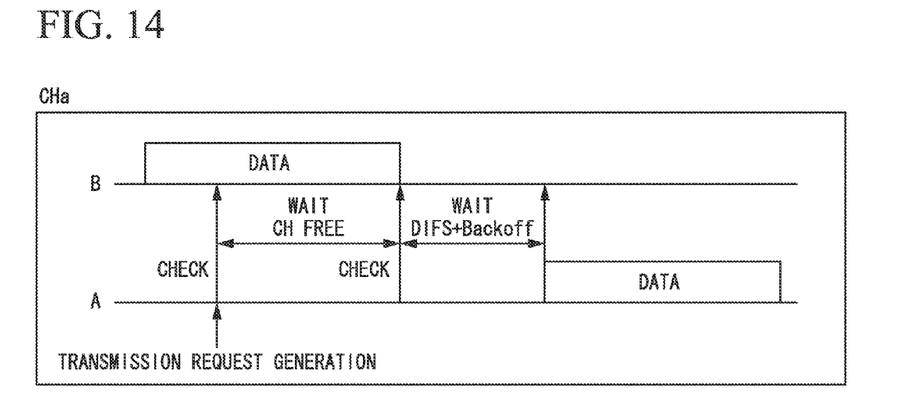
FIG. 14 is a sequence diagram that shows a communication sequence in CSMA/CA.
Figure 15:
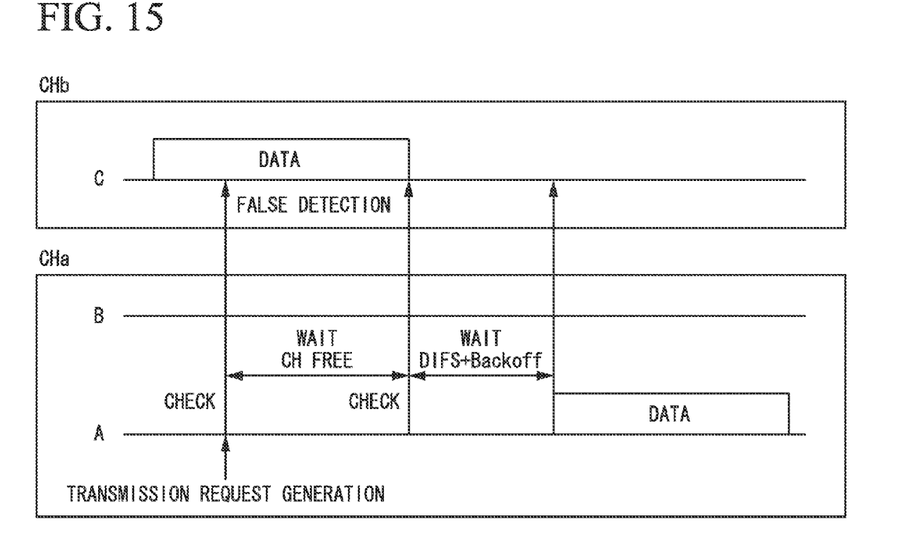
FIG. 15 is a sequence diagram that shows an example of false detection of a signal of an adjacent communication channel.

Generally, in data communication of a communication channel that is set to a wireless terminal, transmission control of data is performed by CSMA/CA (Carrier Sense Multiple Access with Collision Avoidance). FIG. 14 shows the communication sequence of this method. When transmitting a transmission frame, a wireless terminal A confirms the usage state of communication channel CHa. As a result, when the communication channel CHa is determined to be in use (busy state), processing is performed to avoid a collision of transmission frames by stopping the transmission of transmission frames until the wireless terminal B that is performing the current frame transmission completes the transmission.

For this reason, in the case of the usage state of communication channels determined at the start of communication changing during data communication, such as a rapid increase in the amount of data communication of another wireless terminal due to the start of file transmission by a PC or the like, there may have been an influence on the transmission, such as the probability of a busy state of the communication channel occurring increasing, and the transmission rate falling. In contrast to this, Japanese Unexamined Patent Application, First Publication 2006-109448 (hereinbelow referred to as Patent Document 2) provides a wireless LAN system that calculates a receiving rate of frames including another BSSID different from a corresponding BSSID among the whole received frames, detects whether or not interference takes place between the BSSs on the basis of the this receiving rate, and changes the communication channel.

SUMMARY OF THE INVENTION

An image transmitting device according to the present invention includes: a transmitting unit that transmits image data by wireless communication; a measuring unit that measures information relating to a busy state of a communication channel used in the wireless communication for a time period per 1 field of the image data; and a judging unit that judges a state of the communication channel based on a measurement result by the measuring unit.

Also, in the image transmitting device of the present invention, the measuring unit may measure a busy time per 1 field of the image data of the communication channel, and a data retransmission rate per 1 field of the image data.

Also, in the image transmitting device of the present invention, with the data retransmission rate per 1 field of the image data expressed as Er, the judging unit may judge the state of the communication channel by comparing the busy time per 1 field of the image data of the communication channel with time of the 1 field of the image data−{data amount per 1 field of the image data/transmission rate×(1+Er)}.

An image communication system according to the present invention includes an image transmitting device and an image receiving device. The image transmitting device includes: a first transmitting unit that transmits image data by wireless communication; a measuring unit that measures information relating to a busy state of a communication channel used in the wireless communication for a time period per 1 field of the image data; a judging unit that judges a state of the communication channel based on a measurement result by the measuring unit; and a second transmitting unit that transmits, by wireless communication, notification information notifying of a change of a communication channel in accordance with a judgment result by the judging unit. The image receiving device includes: a first receiving unit that receives the image data by wireless communication; a second receiving unit that receives the notification information by wireless communication; and a changing unit that changes the communication channel used in the wireless communication in a case of the notification information being received.

DETAILED DESCRIPTION OF THE INVENTION

Figure 1:
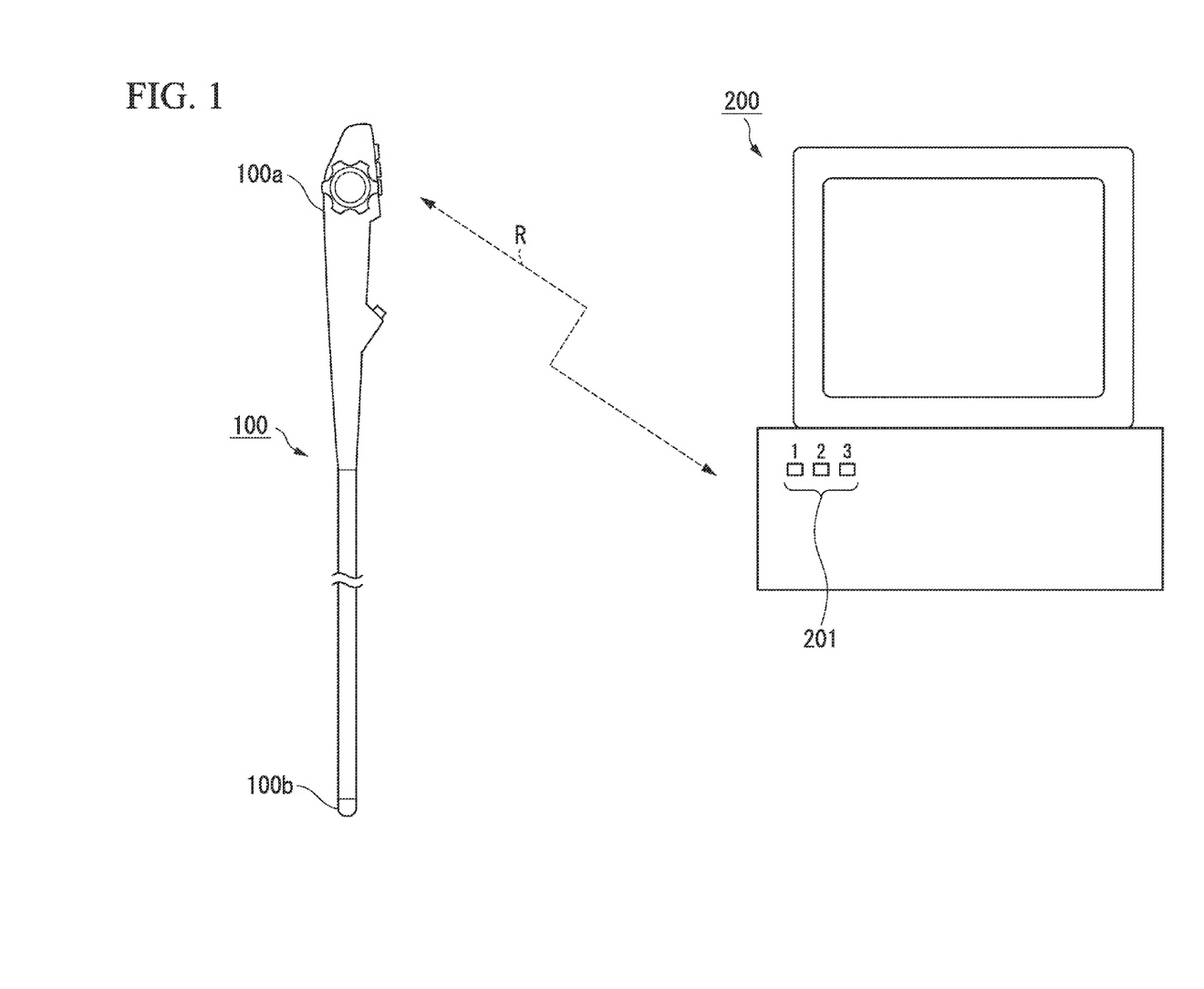
FIG. 1 is a configuration view that shows a constitution of an endoscope device according to one embodiment of the present invention.

Hereinbelow, an embodiment of the present invention shall be described with reference to the drawings. FIG. 1 shows a constitution of an endoscope device (image communication system) according to the present embodiment. The present endoscope device is constituted from an endoscope 100 (transmitter: image transmitting device), and a receiving device 200 (receiver: image receiving device). The endoscope 100 transmits the image data that has been taken by wireless communication (radio waves R). The receiving device 200 receives the image data transmitted from the endoscope 100, and displays images on a monitor. The endoscope 100 includes an operating unit 100a that is comprised by a plurality of switches for the operator to input operation instructions. The receiving device 200 includes an ID display unit 201 that is comprised by a plurality of LEDs that show the ID set state.

Figure 2:
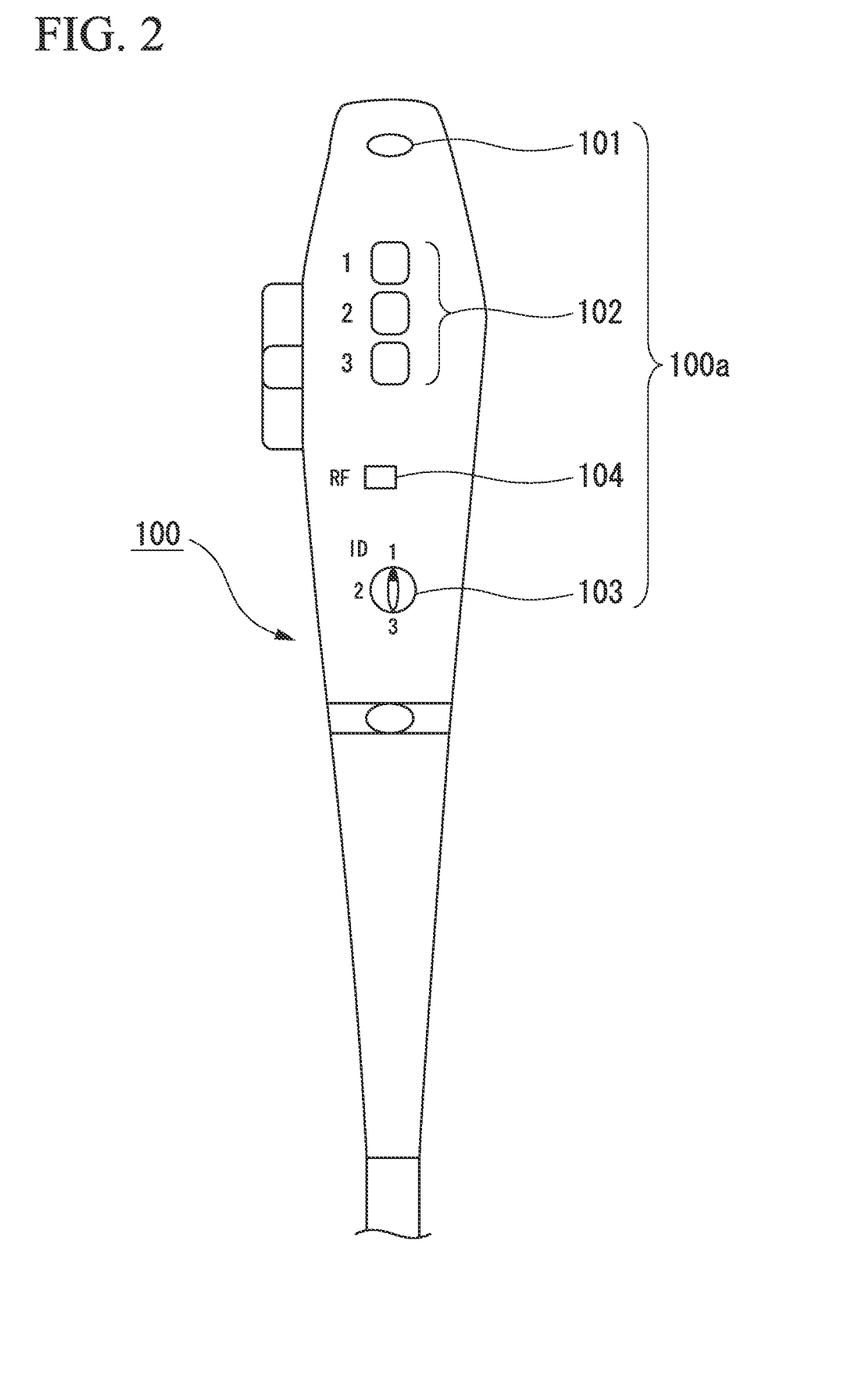
FIG. 2 is an external view of an endoscope according to the embodiment of the present invention.

FIG. 2 shows the endoscope 100 in the state seen from the face on which the operation switches are arranged. The operating unit 100a of the endoscope 100 includes a power switch 101, a plurality of operation switches 102, an ID setting switch 103, and a state display LED 104. The ID setting switch 103 is a switch that sets the ID for pairing with the receiving device 200 that is to perform communication with the endoscope 100. A plurality of IDs are prepared, and it is possible to set an arbitrary ID. Although not shown in FIG. 1, a switch that sets the ID is also provided in the receiving device 200. Connection is possible with the receiving device 200 in which the same ID as the ID that is set at the endoscope 100 is set.

Figure 3:
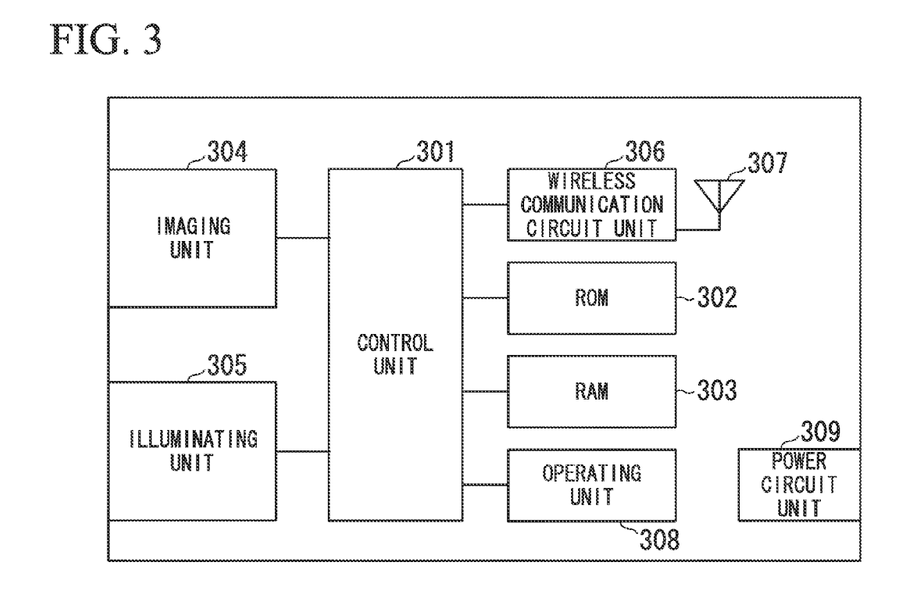
FIG. 3 is a block view that shows a constitution of the endoscope according to the embodiment of the present invention.

FIG. 3 shows a electrical constitution of the endoscope 100. The endoscope 100 is constituted from a control unit 301 (measuring unit, judging unit), a ROM 302, a RAM 303, an imaging unit 304, an illuminating unit 305, a wireless communication circuit unit 306 (transmission unit), an antenna 307, an operating unit 308, and a power circuit unit 309.

The control unit 301 operates according to a program that is stored in the ROM 302, and controls the operation sequence of the endoscope 100. The ROM 302 is a nonvolatile memory, such as Flash ROM. Various setting information including program data for control of the endoscope 100, communication setting parameters, and various setting information is stored in the ROM 302. The communication setting parameters include the communication channel (frequency), SSID (Service Set Identifier), WEP (Wired Equivalent Privacy) and the like. The content of the communication channel settings table shall be described later.

The RAM 303 is used as an area that temporarily stores a buffer that temporarily buffers the image data that is output from the imaging unit 304, a work area used for calculation and the like of the control unit 301, various settings, and the like.

The imaging unit 304 is constituted from a lens that images incident light, a photoelectric transducer (CCD, CMOS sensor, or the like) that converts the imaged light into an electrical signal, and an AD converter (analog-digital converter) that converts the analog electrical signal that is output from the photoelectric converter to a digital electrical signal.

The illuminating unit 305 is constituted from an illumination lens, an LED, an LED drive circuit and the like, and is arranged at a distal end unit 100b of the endoscope 100 (refer to FIG. 1). The light that is emitted from the LED is radiated on the part to the observed in a body cavity via the illumination lens. The arrangement of the LED is not limited to the distal end unit 100b. A constitution is also possible that arranges the LED in the interior of the operating unit 100a, and guides the light to the distal end unit 100b by a light guide.

The wireless communication circuit unit 306 is constituted from a high-frequency circuit unit that is required for wireless communication, an encoding/decoding circuit, a buffer memory, and the like. The antenna 307 is connected to the wireless communication circuit unit 306. In the present embodiment, as one example of a wireless communication method, IEEE 802.11 is used. In order to carry out wireless communication with the receiving device 200, it is necessary to perform the setting of the same communication channel, SSID and the like as the communication channel, SSID and the like that have been set for the receiving device 200.

The operating unit 308 (corresponding to the operating unit 100*a* of FIG. 1) has the power switch 101, the operation switches 102, and the ID setting switch 103 shown in FIG. 2, and outputs the states and state changes of these buttons and switches as electrical signals. Also, the state display LED 104 that reports the connection state with the receiving device 200 is arranged in the operating unit 308.

A power circuit unit 309 is constituted from a battery, and a DC-DC converter, and the like. The power circuit unit 309 supplies electricity to each of the aforementioned blocks by detecting that the power switch 101 has been turned ON.

Figure 4:
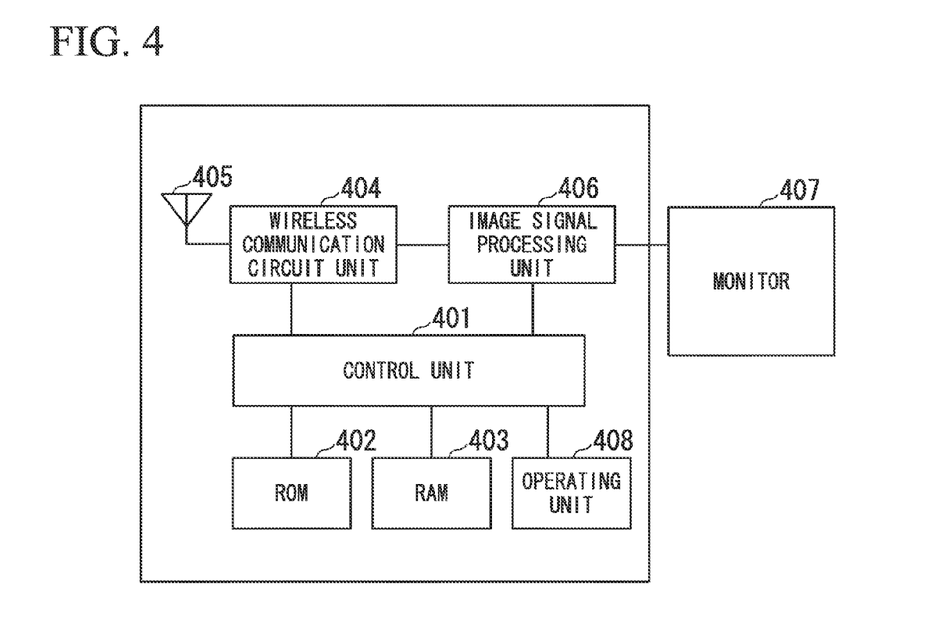
FIG. 4 is a block view that shows a constitution of a receiving device according to the embodiment of the present invention.

FIG. 4 shows an electric configuration of the receiving device 200. The receiving device 200 is constituted from a control unit 401 (changing unit), a ROM 402, a RAM 403, a wireless communication circuit unit 404 (receiving unit), an antenna 405, an image signal processing unit 406, a monitor 407, and an operating unit 408.

The control unit 401 operates according to the program stored in the ROM 402, and controls the operation sequence of the receiving device 200. The ROM 402 is a non-volatile memory such as flash ROM. Program data for control of the receiving device 200, various setting information that includes communication setting parameters, a communication channel settings table, and a search table are stored in the ROM 402. The communication channel settings table and the search table will be described in detail below.

The RAM 403 is used as an area that temporarily stores a buffer that temporarily buffers the image data that is received by the wireless communication circuit unit 404, a work area used for calculation and the like of the control unit 301, various settings, and the like.

The wireless communication circuit unit 404 is constituted from a high-frequency circuit unit that is required for wireless communication, an encoding/decoding circuit, a buffer memory, and the like. The antenna 405 is connected to the wireless communication circuit unit 404. The wireless communication circuit unit 404 performs wireless communication in accordance with the wireless LAN protocol in the same manner as the wireless communication circuit 306 of the endoscope 100.

The image signal processing unit 406 converts the image data that is received by the wireless communication circuit unit 404 to an NTSC signal or a PAL signal, and outputs it to the monitor 407. The monitor 407 is constituted from a liquid crystal display device and a control circuit therefor. The monitor 407 performs display of images, and operates as the reporting unit that reports the state of the wireless connection.

Although not shown in FIG. 1, the operating unit 408 has an ID setting switch that is mounted on the back face of the receiving device 200. The operating unit 408 outputs as an electrical signal a signal that shows the ID corresponding to the set state of the ID setting switch. Also, the ID display unit 201 that displays by LEDs the ID that has been selected by the ID setting switch is arranged in the operating unit 408 (refer to FIG. 1).

Figure 10:
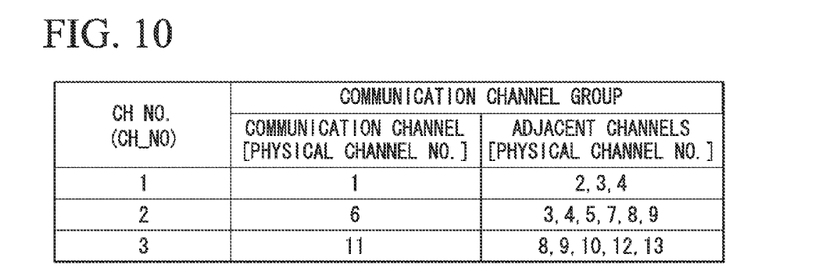
FIG. 10 is a reference diagram that shows contents of communication channel settings table in the embodiment of the present invention.

FIG. 10 shows the content of the communication channel settings table. In the communication channel settings table, a communication channel number is associated with a CH number (CH_NO) that identifies a communication channel group. In IEEE 802.11, wireless communication can be performed by selecting an arbitrary communication channel from a plurality of communication channels. The center frequencies of the communication channels are separated by 5 MHz. However, since each communication channel uses a frequency band of approximately 20 MHz, overlapping of frequency bands that are used occurs between adjacent communication channels.

In the present embodiment, 13 communication channels are prepared. Those 13 communication channels belong to at least any of the three communication channel groups that correspond to each CH number. For example, the communication channel group including communication channels 1, 2, 3, and 4 correspond to CH number 1. The communication channel group including communication channels 3, 4, 5, 6, 7, 8, and 9 correspond to CH number 2. The communication channel group including communication channels 8, 9, 10, 11, 12, and 13 correspond to CH number 3.

Figure 12:
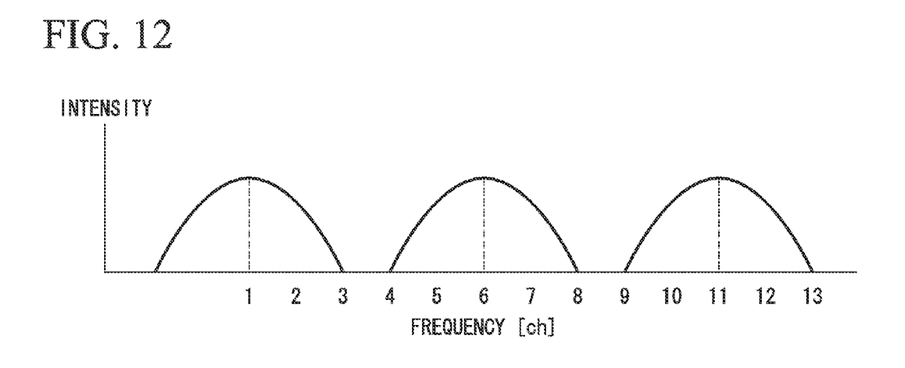
FIG. 12 is a reference diagram that shows frequency bands that communication channels use.

One communication channel among the communication channels that belong to each communication channel group is used for a logical connection described later. For example, in the communication channel group that corresponds to CH number 1, the communication channel 1 is used for a logical connection. In the communication channel group that corresponds to CH number 2, the communication channel 6 is used for a logical connection. In the communication channel group that corresponds to CH number 3, the communication channel 11 is used for a logical connection. As shown in FIG. 12, the frequency bands of the communication channels 1, 6, and 11 do not mutually overlap. One communication channel group includes one communication channel that is used for a logical connection (described as the communication channel in FIG. 10), and communication channels in which the used frequency band partially overlaps with this communication channel (described as adjacent channels in FIG. 10).

Stating the above in more general terms, n (n>1) communication channels in which the frequency band partially overlaps with at least one other communication channel is prepared, and x (1<x≤n) communication channel groups are prepared of which L (1≤L<n) communication channels belong. In the example shown in the present embodiment, n=13, L=4 (CH number 1), 7 (CH number 2), 6 (CH number 3), and x=3.

Figure 11:
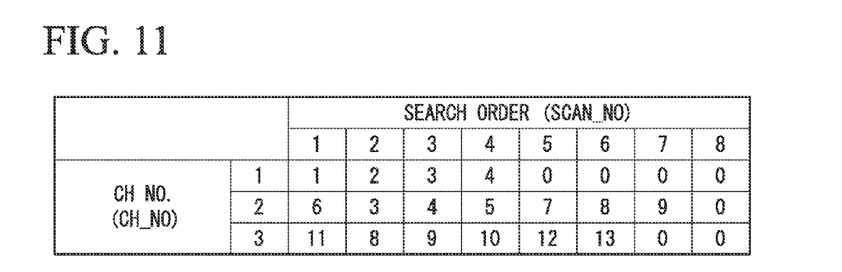
FIG. 11 is a reference diagram that shows contents of a search table in the embodiment of the present invention.

FIG. 11 shows the content of the search table. In the search table, for each CH number, the search order and the communication channel numbers that belong to each communication channel group are associated. There are search orders in which "0" is stored as a communication channel number. This "0" is a value that is used for judging the completion of the search phase described later. In the search phase, the usage states of communication channels are detected in a sequence following the search order.

Next, the operation of the endoscope device according to the present embodiment shall be described. In the present embodiment, it is assumed that after powering on the receiving device 200 being used, the operator powers on the endoscope 100 being used. Hereinbelow, the operation of the endoscope 100 shall be described with reference to FIG. 5 and FIG. 6. After performing the ID setting by the ID setting switch 103 of the endoscope 100 in accordance with the ID displayed by the ID display unit 201 of the receiving device 200, the operator powers on the endoscope 100. When the endoscope 100 is powered on, the control unit 301 initializes each function block of the endoscope 100 (Step S501). Then, the control unit 301 initializes the parameter CH_NO, which shows the CH number, to 1 (Step S502).

Figure 5:
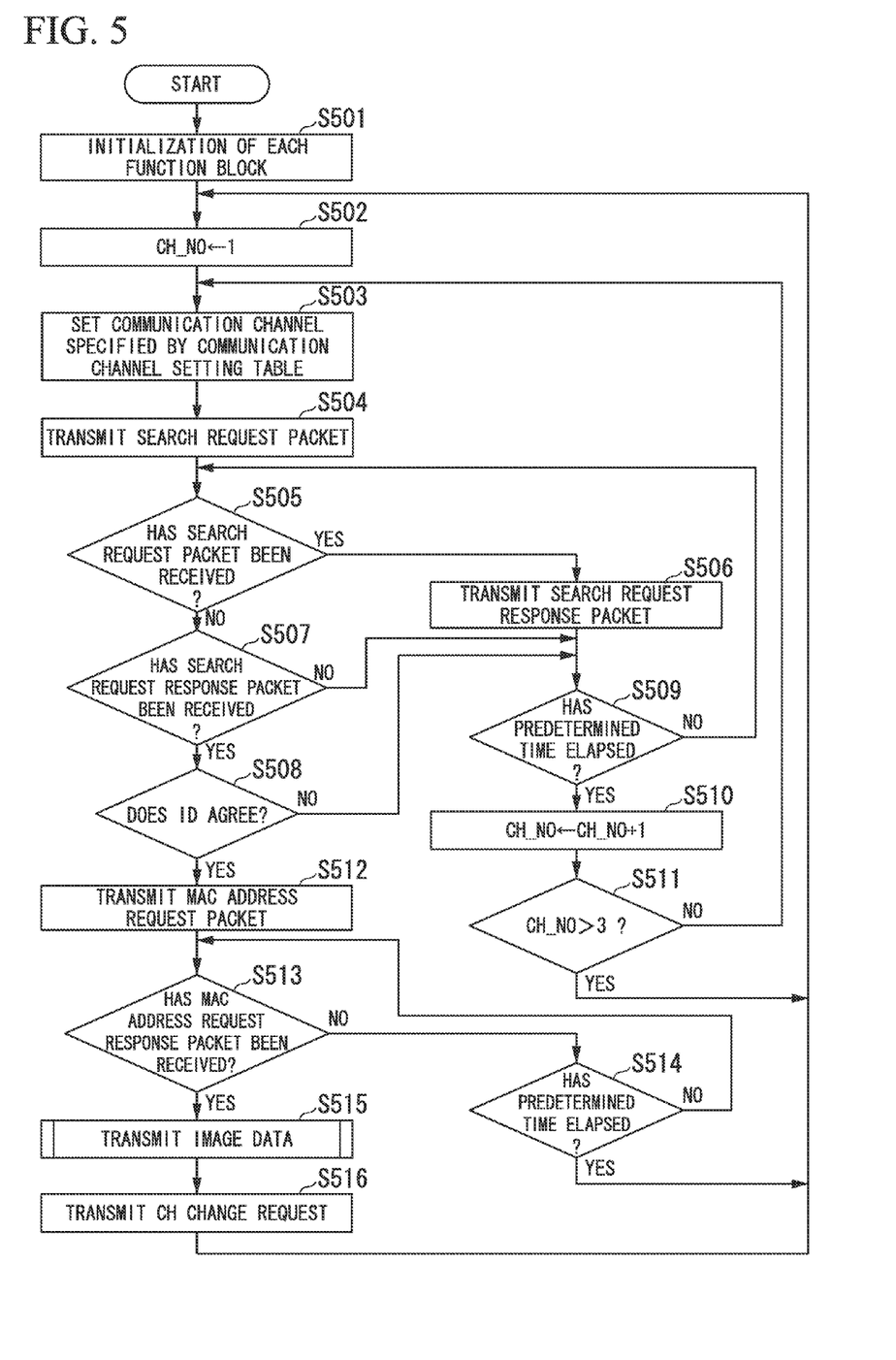
FIG. 5 is a flowchart that shows an operation of the endoscope according to the embodiment of the present invention.

Then, the endoscope 100 performs a physical connection of wireless communication in the following manner. In the physical connection, the wireless frequency and the SSID to be used in the connection at the physical layer are determined, and the packets to be transmitted and received to/from the communication partner are put in a state that can be fetched on hardware. Specifically, the endoscope 100 transitions to a search phase of the wireless communication terminal Upon transitioning to the search phase, the control unit 301 reads out the numbers of the communication channels (any of communication channels 1, 6, 11) specified by the parameter CH_NO in the communication channel settings table, and reads out the communication setting parameter corresponding to the communication channel of that number from the ROM 302 and sets it to the wireless communication circuit unit 306 (Step S503). During the initial operation after power on, the communication setting parameter corresponding to the communication channel 1 is set.

In the search of a wireless communication terminal, a search request packet is transmitted, and the reception of a search request response packet corresponding to the search request packet is performed for a predetermined period. For this reason, the control unit 301 causes the wireless communication circuit unit 306 to transmit the search request packet by broadcast (Step S504).

The control unit 301, after the transmission of the search request packet, judges whether or not it has received a search request packet from another wireless communication terminal (Step S505). In the case of the wireless communication circuit unit 306 having received the search request packet, the control unit 301 causes the wireless communication circuit unit 306 to transmit a search request response packet to the transmission source of the search request packet (Step S506). In the search request response packet of the present embodiment, the ID that is set by the ID setting switch is included. In the case of the wireless communication circuit unit 306 having not received the search request packet, the control unit 301 judges whether or not it has received the search request response packet (Step S507).

In the case of the wireless communication circuit unit 306 having received the search request response packet, the control unit 301 compares the ID set by the ID setting switch 103 and the ID included in the search request response packet, and judges whether or not both agree (Step S508). As described below, the receiving device 200 detects the usage state of each communication channel while changing the communication channels in sequence in the search phase. In the case of the receiving device 200 that is to be connected using the same communication channel as the communication channel that is set to the endoscope 100, the search request response packet that includes the same ID as the ID that is set by the ID setting switch 103 is received. Accordingly, by performing a judgment based on the ID, it is possible to confirm that the receiving device 200 to be connected exists. In the case of the ID that is set by the ID setting switch 103 and the ID included in the search request response packet agreeing, the processing proceeds to Step S512.

The case of sending a search request response packet in Step S506, the case of not receiving a search request response packet in Step S507, and the case of the ID set by the ID setting switch 103 and the ID that is included in the search request response packet not agreeing shall be explained. In these cases, the control unit 301 judges whether or not a predetermined time has elapsed after sending the search request packet in Step S504 (Step S509). In the case of the predetermined time having not elapsed, the process returns to Step S505. In the case of the predetermined time having elapsed, the control unit 301, by adding "1" to the value of the parameter CH_NO, updates the value of CH_NO (Step S510).

Then, the control unit 301 judges whether or not the value of the parameter CH_NO has exceeded "3" (Step S511). In the case of the value of the parameter CH_NO exceeding "3", the process returns to Step S502. In the case of the value of the parameter CH_NO not exceeding "3", the process returns to Step S503.

On the other hand, in Step S508, in the case of the ID set by the ID setting switch 103 and the ID included in the search request response packet agreeing, the endoscope 100 transitions to the logical connection phase. In order to establish a logical connection, the control unit 301 causes the wireless communication circuit unit 306 to send a MAC address request packet to the receiving device 200 (Step S512). After the sending of the MAC address request packet, the control unit 301 judges whether or not it has received a MAC address request response packet from the receiving device 200 (Step S513).

As described below, in the receiving device 200, as the communication channel used for image data communication with the endoscope 100, a communication channel is selected in which radio-wave interference with the communication channels that surrounding wireless communication terminals are using is not easily generated. After this communication channel is selected, in the case of the MAC address request packet being received, the receiving device 200 returns a MAC address request response packet. In the case of the same communication channel being set to the endoscope 100 and the receiving device 200, the MAC address request response packet from the receiving device 200 is received by the endoscope 100.

In the case of receiving the MAC address request response packet, the logical connection is completed. By the transmission and reception of the MAC address request packet and the MAC address request response packet, MAC addresses are exchanged between the endoscope 100 and the receiving device 200. When this logical connection is completed, among the plurality of communication terminals that are physically connected, two specified wireless communication terminals, that is, the combination of the endoscope 100 and the receiving device 200, enter an established state, and the address that the endoscope 100 transmits image data (MAC address) is established.

Then, the wireless communication circuit unit 306 starts the transmission of image data to the receiving device 200 (Step S515). The details of the process in Step S515 will be given later. In Step S515, the state of the communication channel that is being used for transmission of the image data is detected, and based on that state it is judged whether or not to change the communication channel. In the case of being judged to change the communication channel, the control unit 301 causes the wireless communication circuit unit 306 to transmit a CH change request that gives notice of a change of the communication channel to the receiving device 200 (Step S516). After the transmission of the CH change request, the process returns to Step S502.

On the other hand, in the case of not receiving a MAC address request response packet in Step S513, the control unit 301 judges whether or not a predetermined time from after sending the MAC address request packet in Step S512 has elapsed (Step S514). In the case of the predetermined time having elapsed, the process returns to Step S502. Also, in the case of the predetermined time not having elapsed, the process returns to Step S513.

Figure 6:
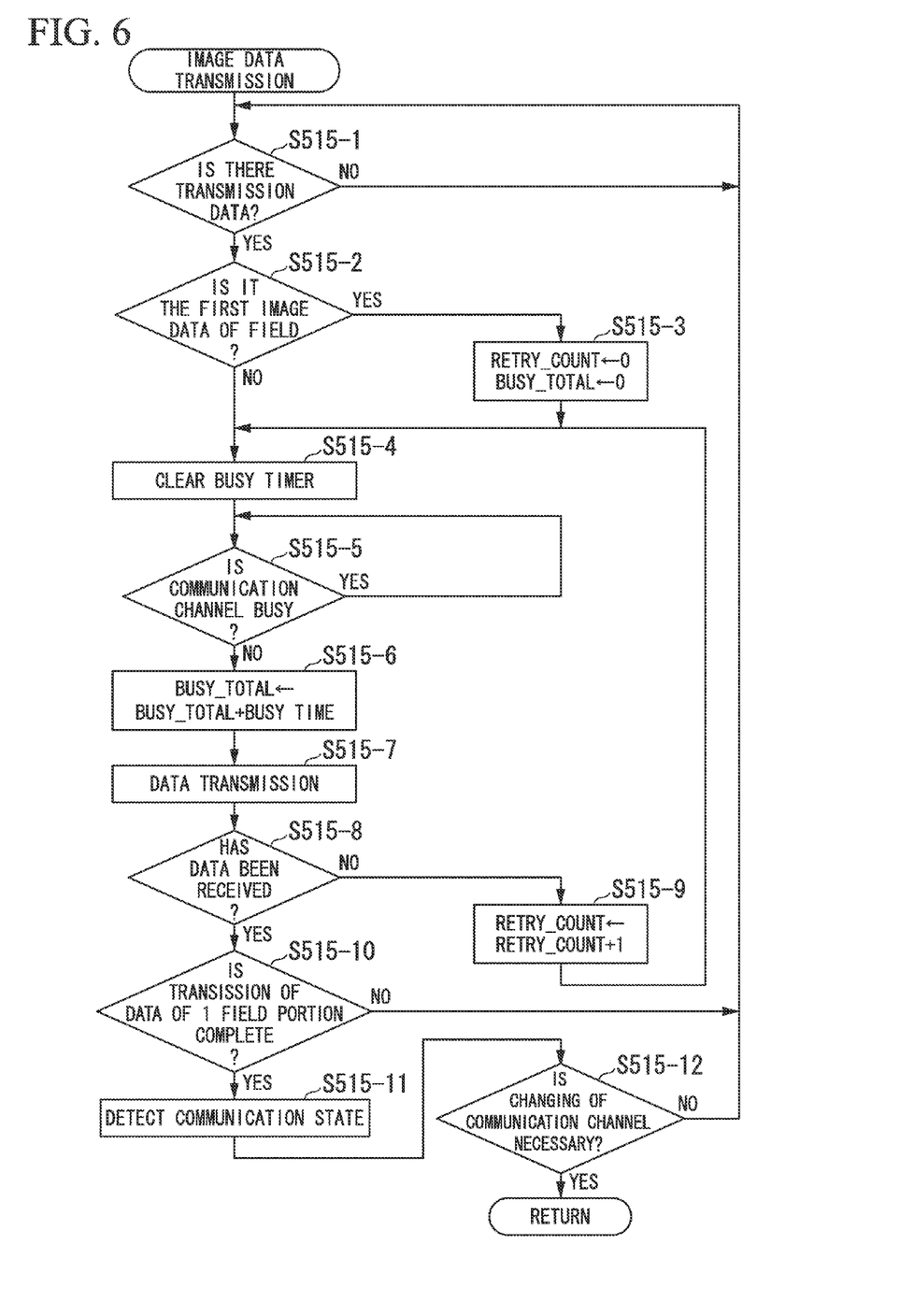
FIG. 6 is a flowchart that shows an operation of the endoscope according to the embodiment of the present invention.

FIG. 6 shows the details of the process in Step S515. The image data that is generated by the imaging unit 304 is successively accumulated in a buffer memory on the RAM 303, in the format of transmission data of a fixed length in which the field number and a number showing the position in the field (1 to N) are included. The control unit 301 judges whether or not image data that should be sent is in the buffer memory (Step S515-1). In the case of there being no image data that should be sent, the control unit 301 again performs the judgment of Step S515-1. Also, in the case of there being image data that should be sent, the control unit 301 judges whether or not that image data is the first image data of the field (Step S515-2).

In the case of the image data being the first image data of the field, the control unit 301 initializes the parameters used for subsequent control (RETRY_COUNT, BUSY_TOTAL) (Step S515-3). RETRY_COUNT is a parameter that shows the number of retransmissions, and is used for calculation of the data retransmission rate. The value of RETRY_COUNT is set to "0" during initialization. BUSY_TOTAL is a parameter that shows the total of the time in which the communication channel is busy (busy time), and is used for judgment of the communication state. The value of BUSY_TOTAL is set to "0" during initialization.

In the case of the image data not being the first image data of the field, the process of Step S515-3 is skipped. Then, the control unit 301 clears the busy timer that it is equipped with (Step S515-4). The busy timer is started directly after being cleared, and starts measurement of the busy time. The control unit 301 measures the busy time by this busy timer.

Then, the control unit 301 confirms the state of the communication channel, and judges whether or not the communication channel is in a busy state (Step S515-5). In the case of the communication channel being in a busy state, the control unit 301 again performs the judgment of Step S515-5. In the case of the communication channel not being in a busy state, the control unit 301 updates the value of BUSY_TOTAL by adding the time that the busy timer has measured to the value of BUSY_TOTAL at the current point in time (Step S515-6).

Then, the control unit 301 reads out the image data from the buffer memory, and outputs it to the wireless communication circuit unit 306. The wireless communication circuit unit 306 transmits the image data to the receiving device 200 (Step S515-7). The receiving device 200 returns ACK to the endoscope 100 in the case of having received image data. The wireless communication circuit unit 306, in the case of having received ACK, gives notice of the reception of ACK to the control unit 301. After transmission of the image data, the control unit 301 judges whether or not the image data has been received by the receiving device 200 by confirming whether or not ACK has been received by the endoscope 100 (Step S515-8).

In the case where it is confirmed that the image data has not been received by the receiving device 200 due to ACK not being received by the endoscope 100, the control unit 301 updates RETRY_COUNT by adding "1" to the value of RETRY_COUNT (Step S515-9). Then, the process returns to Step S515-1. After this, the image data is retransmitted in Step S515-7. In the case where it is confirmed that the image data has been received by the receiving device 200 due to ACK being received by the endoscope 100, the control unit 301 judges whether or not the transmission of the image data of 1 field portion is completed (Step S515-10).

In the case of the transmission of the image data of 1 field portion not being completed, the process returns to Step S515-1. In the case of the transmission of the image data of 1 field portion being completed, the control unit 301 detects the state of the communication channel that is set at the current point in time (Step S515-11). Specifically, the state of the communication channel is detected in the following manner. First, the control unit 301 calculates the data retransmission rate per 1 field Er by dividing the value of RETRY_COUNT by the transmission data number per 1 field (Eq. (1)).

$$Er = RETRY\_COUNT/\text{transmission data number per 1 field} \quad (1)$$

Next, the control unit 301 calculates the time required for transmission of image data per 1 field portion (transmission time per 1 field) (Eq. (2)).

$$\text{Transmission time per 1 field} = \text{data amount per 1 field}/\text{transmission rate} \times (1+Er) \quad (2)$$

Moreover, the control unit 301 calculates the surplus time in 1 field (Eq. (3)).

$$\text{Surplus time in 1 field} = 1 \text{ field time} - \text{transmission time per 1 field} \quad (3)$$

Following Step S515-11, the control unit 301, by comparing the value of BUSY_TOTAL that shows the busy time per 1 field and the surplus time in 1 field, judges the state of the communication channel, and judges whether or not changing of the communication channel is necessary (Step S515-12). In the case of the value of BUSY_TOTAL exceeding the surplus time in 1 field, since the data transmission of 1 field portion is not completed within 1 field, it is necessary to change the communication channel. In the case of the value of BUSY_TOTAL being equal to or less than the surplus time in 1 field, there is no need to change the communication channel. When the aforementioned Eqs. (1) to (3) are brought together, in the case of the following Eq. (4) being satisfied, changing of the communication channel becomes necessary.

$$BUSY\_TOTAL > 1 \text{ field time} - \{\text{data amount per 1 field}/\text{transmission rate} \times (1+Er)\} \quad (4)$$

As stated above, it is possible to detect the state of a communication channel including the influence due to interference of the data signal of adjacent communication channels on the communication channel being used by detecting the busy time.

In the case of a change of the communication channel being necessary, the process proceeds to Step S516. As stated above, in Step S516, a CH change request that notifies a change of the communication channel is transmitted to the receiving device 200. In the case of a change of the communication channel not being necessary, the process returns to Step S515-1.

In the aforementioned, imaging by the imaging unit 304 was described in the case of being performed per field, but is not limited thereto. The imaging by the imaging unit 304 may be performed per frame.

Figure 7:
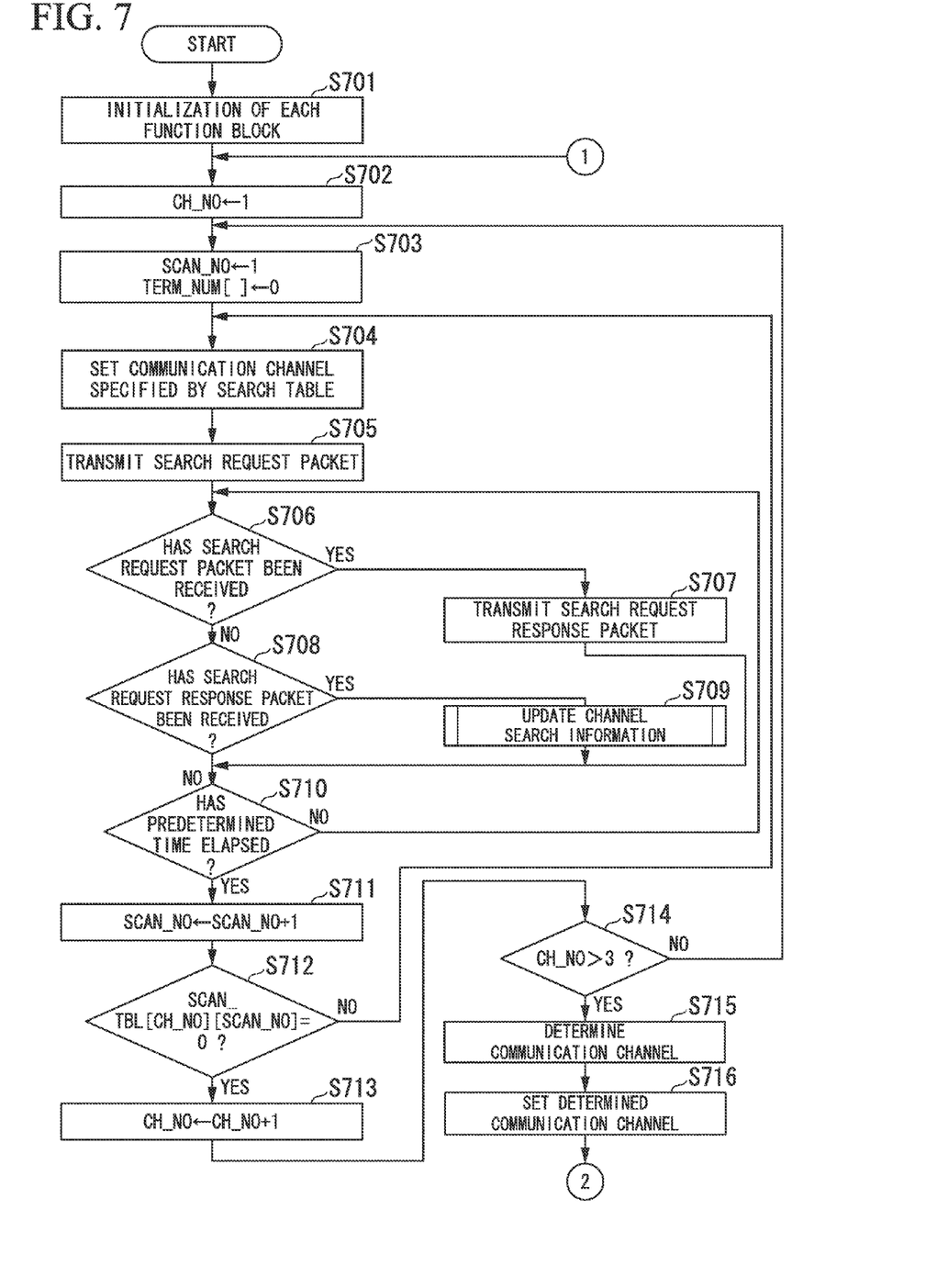
FIG. 7 is a flowchart that shows an operation of the receiving device according to the embodiment of the present invention.
Figure 8:
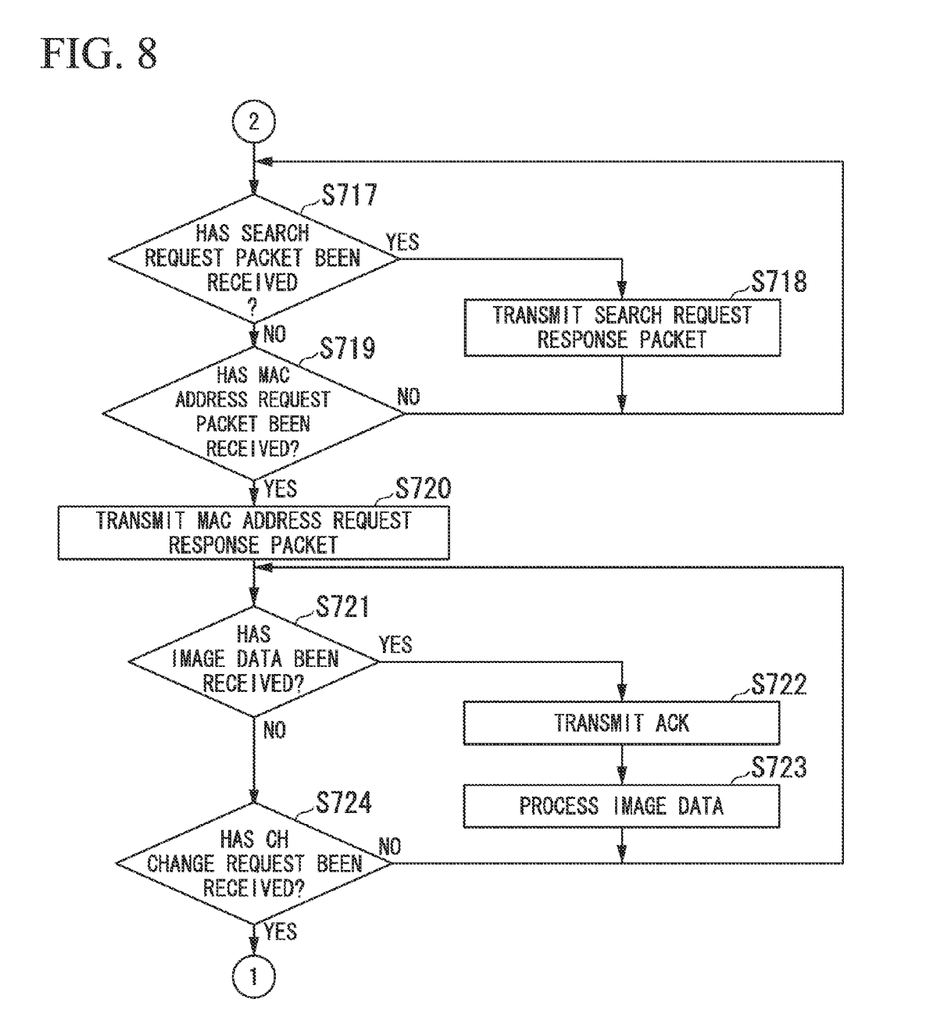
FIG. 8 is a flowchart that shows an operation of the receiving device according to the embodiment of the present invention.
Figure 9:
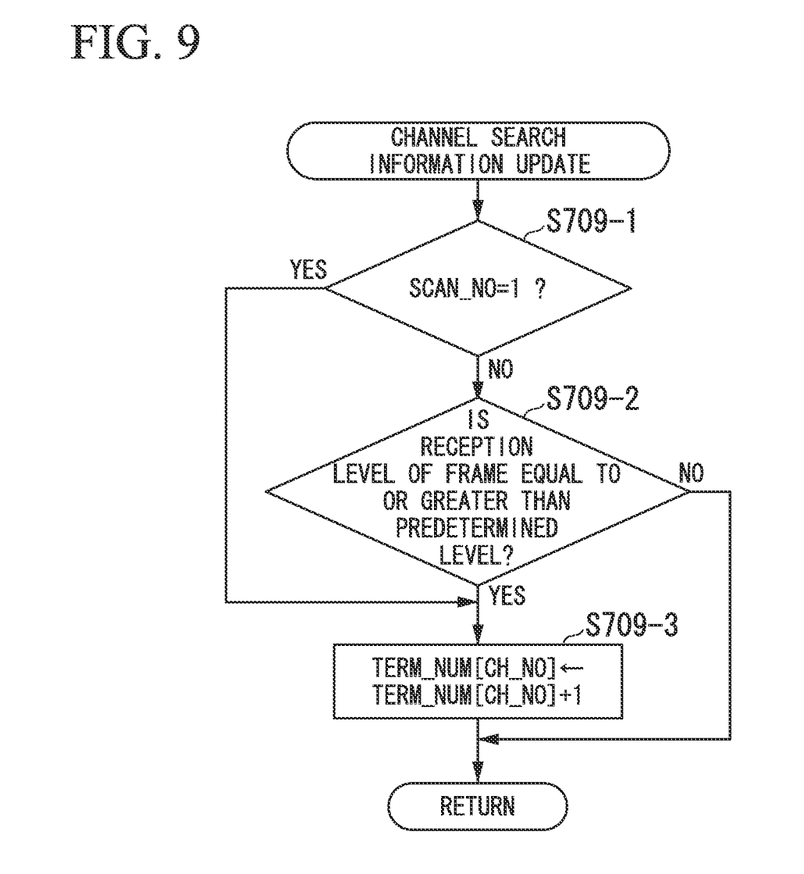
FIG. 9 is a flowchart that shows an operation of the receiving device according to the embodiment of the present invention.

Next, the operation of the receiving device 200 shall be described according to FIG. 7 to FIG. 9. The operator, after performing the setting of the ID by the ID setting switch of the receiving device 200, powers on the receiving device 200. When the power supply of the receiving device 200 is turned on, the control unit 401 initializes each function block of the receiving device 200 (Step S701).

Then, the control unit 401 initializes the parameters used for subsequent control (CH_NO, SCAN_NO, TERM_NUM[ ]) (Step S702 and Step S703). Specifically, in Step S702, the CH_NO is initialized. In Step S703, SCAN_NO, and TERM_NUM[ ] are initialized. CH_NO is a parameter that shows the CH number as described above. During initialization, the value of CH_NO is set to "1". SCAN_NO is a parameter that stores the search sequence in the search table. During initialization, the value of SCAN_NO is set to "1". TERM_NUM[ ] is a parameter that stores the number of surrounding wireless communication terminals using communication channels that satisfy predetermined conditions. During initialization, the value of each parameter of TERM_NUM[ ] is set to "0". TERM_NUM[ ] has the three parameters of TERM_NUM[1], TERM_NUM[2], and TERM_NUM[3].

Then, the receiving device 200 performs physical connection of wireless communication. Specifically, the receiving device 200 transitions to the search phase of the communication channel. Upon transitioning to the search phase, the control unit 401 reads out from the search table the number of the communication channel that is designated by CH_NO and SCAN_NO (communication channel in which CH number is CH_NO, and search order is SCAN_NO), and reads out from the ROM 402 the communication setting parameter corresponding to that communication channel to set it to the wireless communication circuit unit 404 (Step S704). In the search of the communication channel, the search request packet is transmitted, and the reception of the search request response packet to the search request packet is performed for a predetermined period. For this reason the control unit 401 causes the wireless communication circuit unit 404 to transmit by broadcast the search request packet (Step S705). The wireless communication terminal in which the same communication channel as the receiving device 200 is set receives the search request packet that was transmitted from the receiving device 200, and transmits a search request response packet.

The control unit 401 judges whether or not it has received the search request packet from another wireless communication terminal after transmission of the search request packet (Step S706). In the case of the wireless communication circuit unit 404 having received the search request packet, the control unit 401 causes the wireless communication circuit unit 404 to transmit by unicast a search request response packet to the transmission source of the search request packet (Step S707). As described above, the ID designated by the ID setting switch is included in the search request response packet. Thereafter, the process proceeds to Step S710. In the case of the wireless communication circuit unit 404 not receiving the search request packet, the control unit 401 judges whether or not it has received a search request response packet from another wireless communication terminal (Step S708). In the case of receiving the search request response packet, the control unit 401 executes a process that updates the value of TERM_NUM[CH_NO] (channel search information) (Step S709). Thereafter, the process proceeds to Step S710. In the case of the the wireless communication circuit unit 404 not receiving the search request response packet, the process proceeds to Step S710.

FIG. 9 shows the details of the Step S709. The control unit 401 judges whether or not the value of CH_NO is "1" (Step S709-1). In the case of the value of CH_NO being "1", the process advances to Step S709-3. Also, in the case of the value of CH_NO not being "1", the control unit 401 judges whether or not the reception level (reception signal intensity) of the frame of the search request response packet is equal to or greater than a predetermined level (Step S709-2). In the case of the reception level of the frame being equal to or greater than the predetermined level, the process proceeds to Step S709-3. In the case of the reception level of the frame being less than the predetermined level, the process advances to Step S710. In the case of the process having advanced to Step S709-3, the control unit 401 updates the value of TERM_NUM[CH_NO] by adding "1" to the value of TERM_NUM[CH_NO] (Step S709-3). After the process of Step S709-3, the process advances to Step S710.

The value of TERM_NUM[CH_NO] shows the number of surrounding wireless communication terminals that use the same communication channel as either of the communication channels 1, 6, 11, or use a communication channel in which the frequency band used overlaps with either of the communication channels 1, 6, 11. In Step S709-1, in the case of the value of SCAN_NO being "1", another wireless communication terminal uses the same communication channel as either of the communication channels 1, 6, 11. In Step S709-2, in the case of the frame reception level being equal to or greater than a predetermined level, another wireless communication terminal uses a communication channel in which the frequency band used overlaps with either of the communication channels 1, 6, 11. In the present embodiment, a common threshold value is set as the threshold value of the reception level of a frame in each of the adjacent channels, but is not limited thereto. The threshold value of the predetermined reception level may be set for every adjacent channel.

In the case of the process having advanced to Step S710, the control unit 401 judges whether or not the predetermined time has elapsed after transmitting the search request packet in Step S705 (Step S710). In the case of the predetermined time not having elapsed, the process returns to Step S706. Also, in the case of the predetermined time having elapsed, the control unit 401 adds 1 to the value of SCAN_NO, and updates the value (Step S711).

Next, the control unit 401 reads out from the search table the number of the communication channel that is designated by CH_NO and the updated SCAN_NO (the communication channel in which CH number is CH_NO, and search order is SCAN_NO), and judges whether that number is "0" or not (Step S712). In the case of the number of the communication channel that is designated by CH_NO and the updated SCAN_NO not being "0", the process returns to Step S704. In the case of the communication channel that is designated by CH_NO and the updated SCAN_NO being "0", the control unit 401 updates the value of CH_NO by adding "1" to the value of CH_NO (Step S713).

Then, the control unit 401 judges whether or not the value of CH_NO has exceeded "3" (Step S714). In the case of the value of CH_NO not exceeding "3", the process returns to Step S703. In the case of the value of CH_NO exceeding "3", the control unit 401 determines the communication channel to be used based on the value of TERM_NUM[CH_NO]. Specifically, the control unit 401 compares the wireless communication terminal numbers (TERM_NUM[1], TERM_NUM[2], TERM_NUM[3]) aggregated in Step S709, and determines the communication channel corresponding to the smallest wireless communication terminal number as the communication channel to be used in the logical connection (Step S715).

Specifically, in the case of TERM_NUM[1] being the smallest, communication channel 1, which corresponds to CH number 1, is selected. In the case of TERM_NUM[2] being the smallest, communication channel 6, which corresponds to CH number 2, is selected. In the case of TERM_NUM[3] being the smallest, communication channel 11, which corresponds to CH number 3, is selected. In this way, by using the communication channel that corresponds to the smallest value of TERM_NUM[CH_NO] (CH_NO=1, 2, 3), it is possible to select the communication channel with the optimal communication state. After determination of the communication channel, the control unit 401 reads out from the ROM 402 the communication setting parameter corresponding to the decided communication channel, and sets it to the wireless communication circuit unit 404 (Step S716).

Then, the receiving device 200 transitions to the logical connection phase. The control unit 401 judges whether or not it has received a search request packet from another wireless communication terminal (Step S717). In the case of the wireless communication circuit unit 404 having received a search request packet, the control unit 401 causes the wireless communication circuit unit 404 to transmit by unicast a search request response packet to the transmission source of the search request packet (Step S718). Then, the process returns to Step S717. In the case of the wireless communication circuit unit 404 not having received a search request packet, the control unit 401 judges whether or not it has received the MAC address request packet from the endoscope 100 (Step S719).

In the case of the wireless communication circuit unit 404 not having received the MAC address request packet, the process returns to Step S717. In the case of the wireless communication circuit unit 404 having received the MAC address request packet, the control unit 401 causes the wireless communication circuit unit 404 to transmit the MAC address request response packet to the endoscope 100 (Step S720). Then, the control unit 401 decides whether or not it has received the image data (Step S721). The wireless communication circuit unit 404, in the case of having received the image data, informs the control unit 401 of having received the image data.

In the case of the wireless communication circuit unit 404 having received image data, the control unit 401 causes the wireless communication circuit unit 404 to transmit ACK to the endoscope 100 (Step S722). After transmission of ACK, the image signal processing unit 406 processes the received image data, and output it to the monitor 407. The monitor 407 displays an image based on the image data (Step S723). Then, the process returns to Step S721.

In the case of the wireless communication circuit unit 404 not having received the image data, the control unit 401 judges whether or not it has received a CH change request from the endoscope 100 (Step S724). In the case of the wireless communication circuit unit 404 having received the CH change request, it gives notice of reception of the CH change request to the control unit 401. In the case of having received the CH change request, the process returns to Step S702. The control unit 401 by again executing the process from Step S702 performs changing of the communication channel. In the case of the wireless communication circuit unit 404 not having received the CH change request, the process returns to Step S721.

In the aforementioned operation, the control unit 401 during the initial operation selects the communication channel group that is specified by the CH number (CH NO) (Step S704). Also, the control unit 401 detects as the use state of a communication channel the number of surrounding wireless communication terminals that are using the same communication channel as either of the communications channels 1, 6, 11 that belongs to that communication channel group, or using a communication channel in which the frequency band used overlaps with either of the communication channels 1, 6, 11 (Step S705 to S714). Moreover, the control unit 401, based on the detection results of the use states of the communication channels, determines the communication channel to be used in the logical connection (Step S715).

In this way, by detecting the use states of only the communication channels that belong to a communication channel group, it is possible to efficiently select a communication channel with a good communication state. Also, in Step S715, since a communication channel is selected in which radio-wave interference with the communication channels that surrounding wireless communication terminals are using is not easily generated, it is possible to reduce the generation of communication errors. Also, by performing with the receiving device 200 a process that detects the use state of each communication channel while changing the communication channels, it is possible to achieve power saving of the endoscope 100, which is driven by a battery.

As stated above, according to the present embodiment, by measuring information relating to the busy state of a communication channel being used in the wireless communication, it becomes possible to detect the influence stemming from interference by the data signals of adjacent communication channels. Then, by judging the state of the communication channel based on the measurement result, even in the case of there being interference by the data signals of adjacent communication channels, it is possible to more accurately detect the state of the communication channel. Accordingly, it is possible to detect a drop in the communication rate due to for example interference by the data signals of adjacent communication channels.

Also, by judging the communication state by calculating the surplus time in 1 field based on the data retransmission rate per predetermined time (Eq. (3)), and comparing this surplus time with the busy time per predetermined time of the communication channel, it is possible to judge the communication state with a simple calculation.

Also, in the case of judging that the endoscope 100 should change the communication channel, by transmitting a CH change request to the receiving device 200, and the receiving device 200 that has received the CH change request changing the transmission channel, it is possible to perform wireless communication that uses a good communication channel, without the operator performing an operation to change the communication channel.

Hereinabove, the embodiment of the present invention has been described in detail with reference to the drawings, but a specific constitution is not limited to the aforementioned constitution, and design modifications are included in a range that does not depart from the scope of the present invention.

What is claimed is:
1. An image transmitting device comprising:
a transmitting unit that does not wirelessly transmit image data if carrier sense has been performed and a communication channel is in a busy state, that is, the communication channel is used by other terminals, the transmitting unit wirelessly transmitting image data by using the communication channel if the communication channel is in a non-busy state, that is, the communication channel is not used by other terminals;
a measuring unit that measures a time of being in the busy state and a data retransmission rate of the image data every first time period that is allocated to a time of wirelessly transmitting 1 field or 1 frame of the image data; and
a judging unit that judges a state of the communication channel based on a measurement result by the measuring unit,
wherein the transmitting unit transmits a channel change request that notifies a change of the communication channel in a case where the judging unit has judged that changing the communication channel is necessary,
wherein the transmitting unit wirelessly transmits the image data by using CSMA/CA, and
wherein, when the data retransmission rate per the first time period is expressed as Er, the judging unit judges the state of the communication channel by comparing the time when the communication channel is in the busy state in the first time period with the first time period−{data amount per the first time period of 1 field or 1 frame of the image data/transmission rate of the image data×(1+Er)}.

2. An image communication system comprising an image transmitting device and an image receiving device, the image transmitting device comprising:
a transmitting unit that does not wirelessly transmit image data if carrier sense has been performed and a communication channel is in a busy state, that is, the communication channel is used by other terminals, the transmitting unit wirelessly transmitting image data by using the communication channel if the communication channel is in a non-busy state, that is, the communication channel is not used by other terminals;
a measuring unit that measures a time of being in the busy state and a data retransmission rate of the image data every first time period that is allocated to a time of wirelessly transmitting 1field of 1 frame of the image data; and
a judging unit that judges a state of the communication channel based on a measurement result by the measuring unit,
wherein the transmitting unit transmits a channel change request that notifies a change of the communication channel in a case where the judging unit has judged that changing the communication channel is necessary,
wherein the transmitting unit wirelessly transmits the image data by using CSMA/CA, and
wherein, when the data retransmission rate per the first time period is expressed as Er, the judging unit judges the state of the communication channel by comparing the time when the communication channel is in the busy state in the first time period with the first time period−{data amount per the first time period of 1 field or 1 frame of the image data/transmission rate of the image data×(1+Er)};
the image receiving device comprising:
a receiving unit that receives the image data by wireless communication, and that receives the channel change request by wireless communication; and
a changing unit that changes the communication channel used in the wireless communication in a case of the channel change request being received.

3. An image transmitting method, comprising:
wirelessly transmitting image data by using a communication channel if the communication channel is in a non-busy state, that is, the communication channel is not used by other terminals, and not wirelessly transmitting image data if carrier sense has been performed and the communication channel is in a busy state, that is, the communication channel is used by other terminals;
measuring a time of being in the busy state and a data retransmission rate of the image data every first time period that is allocated to a time of wirelessly transmitting 1 field or 1 frame of the image data; and
judging a state of the communication channel based on a measurement result by the measuring; and
transmitting a channel change request that notifies a change of the communication channel in a case where the judging has judged that changing the communication channel is necessary,
wherein the wirelessly transmitting image data includes wirelessly transmitting the image data by using CSMA/CA, and
wherein the judging the state of the communication channel includes, when the data retransmission rate per the first time period is expressed as Er, judging the state of the communication channel by comparing the time when the communication channel is in the busy state in the first time period with the first time period−{data amount per the first time period of 1 field or 1 frame of the image data/transmission rate of the image data×(1+Er)}.

4. A non-transitory machine readable storage medium having stored thereon a computer program that is operated in an image transmitting device including a transmitting unit, the computer program comprising instructions for causing a machine to control the image transmitting device to perform the steps of:
wirelessly transmitting image data, with the transmitting unit, by using a communication channel if the communication channel is in a non-busy state, that is, the communication channel is not used by other terminals, and not wirelessly transmitting image data if carrier sense has been performed and the communication channel is in a busy state, that is, the communication channel is used by other terminals;
measuring a time of being in the busy state and a data retransmission rate of the image data every first time period that is allocated to a time of wirelessly transmitting 1 field or 1 frame of the image data; and
judging a state of the communication channel based on a measurement result by the measuring; and
transmitting, with the transmitting unit, a channel change request that notifies a change of the communication channel in a case where the judging has judged that changing the communication channel is necessary,
wherein the wirelessly transmitting image data includes wirelessly transmitting the image data by using CSMA/CA, and
wherein the judging the state of the communication channel includes, when the data retransmission rate per the first time period is expressed as Er, judging the state of the communication channel by comparing the time when the communication channel is in the busy state in the first time period with the first time period−{data amount per the first time period of 1 field or 1 frame of the image data/transmission rate of the image data×(1+Er)}.

* * * * *